United States Patent

Tanner et al.

Patent Number: 5,981,767
Date of Patent: Nov. 9, 1999

[54] METHOD OF PRODUCING DRY THIOCTIC ACID

[75] Inventors: Herbert Tanner, Hanau; Karlheinz Drauz, Freigericht-Somborn; Gerhard Sator, Dieburg; Horst Bethge, Rodenbach; Roland Möller, Hammersbach; Frank Hubner, Ober-Ramstadt; Thomas Tacke, Friedrichsdorf; Claus Rehren, Aschaffenburg, all of Germany

[73] Assignee: Asta Medica Aktiengesellschaft, Dresden, Germany

[21] Appl. No.: 09/102,758

[22] Filed: Jun. 23, 1998

[30] Foreign Application Priority Data

Jun. 23, 1997 [DE] Germany .............. 197 26 519

[51] Int. Cl.$^6$ .............................................. C07D 333/24
[52] U.S. Cl. ......................................................... 549/79
[58] Field of Search ....................................... 549/79

[56] References Cited

FOREIGN PATENT DOCUMENTS

| 0487986A2 | 3/1992 | European Pat. Off. . |
| 0593896A1 | 4/1994 | European Pat. Off. . |
| 0733363A1 | 9/1996 | European Pat. Off. . |
| 4229914A1 | 10/1994 | Germany . |

OTHER PUBLICATIONS

Schneider, "Physikalisch–chemische Grundlagen der Extraktion mit uberkritischen Gasen", *Angew. Chem.* 90, 1978, pp. 762–774.

*Primary Examiner*—John Kight
*Assistant Examiner*—Raymond Covington
*Attorney, Agent, or Firm*—Cushman, Darby & Cushman, IP Group of Pillsbury, Madison & Sutro LLP

[57] ABSTRACT

The present invention is relative to a method of producing dry thioctic acid in which a raw material in which concentrated thioctic acid is present is treated with liquid or supercritical $CO_2$, thus yielding thioctic acid with low residual solvent contents in a simple industrial method.

12 Claims, 2 Drawing Sheets

METHOD OF PRODUCING DRY THIOCTIC ACID

BACKGROUND OF THE INVENTION

1. Field of the Invention

The present invention is relative to a method of producing dry thioctic acid with the following formula:

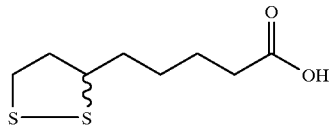

When thioctic acid is mentioned in the present application the enantiomers (R and S form) and the racemic mixture as well as mixtures with any ratio of the enantiomers are to be understood. The exact chemical name of thioctic acid is 1,2-dithiolane-3-pentanoic acid. The (R) enantiomer of thioctic acid is a natural substance which occurs in slight concentrations in practically all animal and vegetable cells. Thioctic acid is of great importance as coenzyme in the oxidative decarboxylation of α-ketocarboxylic acids (e.g. pyruvic acid). Thioctic acid is pharmacologically active and has antiphlogistic and antinociceptive (analgetic) as well as cytoprotective properties. An important medicinal indication is the treatment of diabetic polyneuropathy.

2. Background Information

Thioctic acid is produced according to a number of methods which are described e.g. in J. S. Yadav et al., J. Sci. Ind. Res. 1990, 49, 400; A. G. Tolstikov et al., Bioorg. Khim. 1990, 16, 1670; L. Dasaradhi et al., J. Chem. Soc., Chem. Commun. 1990, 729; A. S. Gopalan et al., J. Chem. Perkin Trans. 1 1990, 1897; A. S. Gopalan et al., Tetrahedron Lett. 1989, 5705; EP 0487986 A2; E. Walton et al., J. Am Chem. Soc. 1995, 77; D. S. Acker and W. J. Wayne, J. Am. Chem. Soc. 1957, 79, 6483; L. G. Chebotareva and A. M. Yurkevich, Khim.-Farm. Zh. 1980, 14, 92. The raw product obtained is then worked up according to customary methods and finally processed to the finished drug. Especially high requirements are placed on the purity of the active substance and of the additives in the approval of the drug; among other things, the residual content of solvent must not exceed a certain value. Recently, there have been attempts to lower this limiting value even more in the case of thioctic acid.

SUMMARY OF THE INVENTION

The invention therefore has the problem of creating a simple industrial method with the aid of which a thioctic acid can be obtained which contains significantly reduced residual contents of solvent in comparison to the state of the art.

The invention solves this problem by a method in which a raw material in which concentrated thioctic acid is present is treated with liquid or supercritical $CO_2$. This can take place batchwise of continuously, during which the CO either flows through or around the raw material, depending on the manner of the workup. The thioctic acid used can stem from any method for producing the same, which method is followed, if necessary, by a customary crystallization and/or extraction. Thioctic acid is customarily crystallized out of a mixture of cyclohexane and ethyl acetate. The crystallized-out thioctic acid is then removed by suction and/or centrifuged. The product obtained can then serve as raw material for the method in accordance with the invention. Alternatively, however, the non-crystallized or extracted product of the production method which is partially or predominantly freed of solvents and impurities can also be used.

A thioctic acid can be obtained in this manner which contains less than 1100 ppm, preferably less than 700 ppm cyclohexane and less than 250 ppm, preferably less than 130 ppm ethyl acetate; the demonstration limit thereby for cyclohexane is approximately 8 ppm and for ethyl acetate approximately 3 ppm. The solvent contents cited are obtained most easily with raw material which is moist with solvent and not thermally pre-dried. Even impurities from the production method in the $CO_2$ can be dissolved [or: "Even impurities can also be dissolved out of the production method in the $CO_2$ . . . "] by selecting suitable conditions, which brings about a depletion of byproducts.

The use of $CO_2$ has the advantage that its critical point of 31.1° C. and 73.8 bar is in a temperature and pressure range which is readily accessible industrially [technically]. In addition, $CO_2$ has the advantages that it is non-combustible and does not endanger the environment. Furthermore, it can be readily separated from the solvent and reused by expanding the mixture of $CO_2$, solvent and, if applicable, impurities accumulating during the treatment, during which the solvent condenses and the impurities separate in solid form, as well as subsequently blowing off the $CO_2$ or returning it to the method after compression. It is possible in the latter instance to work with very little $CO_2$ returned in a cyclic process.

Accordingly, a preferred embodiment of the invention consists of a method in which liquid or supercritical $CO_2$ flows through and/or around solid raw material. In this manner a type of solid-liquid extraction takes place in which the solvent is extracted from the raw material and is dissolved in the liquid or supercritical $CO_2$.

Alternatively, the raw material, dissolved in a solvent, is supplied to a container and at the same time liquid or supercritical $CO_2$ conducted in a countercurrent through the container. A concentration gradient of the $CO_2$ forms thereby in the mixture of thioctic acid/solvent/$CO_2$; as the $CO_2$ content increases the solubility of the thioctic acid decreases until the latter crystallizes out and precipitates on the container wall. The content of cyclohexane can be reduced in this way to especially low values below 20 ppm. This variant can be structured in an especially economical manner so that product obtained from the method of production is dissolved without further workup in a solvent or a solvent mixture and the solution obtained used as raw material, so that the previously customary, expensive crystallization with subsequent removal by suction and centrifuging is eliminated.

The solid, purified thioctic acid is retained in both variants, extraction and crystallization, by a suitable device so that it is not entrained with the current of $CO_2$.

The method is carried out according to the invention at a temperature in a range of 20 to 50° C. Below 20° C. the drying lasts too long, so that the economy of the method is adversely affected whereas at a temperature above 50° C. the tendency of the thioctic acid to polymerize becomes too great.

According to another preferred embodiment of the invention the treatment with liquid or supercritical $CO_2$ is carried out at a pressure in a range of 50 to 1000 bar. The upper limit of this range results from the fact that the solubility of thioctic acid in $CO_2$ increases as the pressure rises. In most instances, especially at temperatures of 35 to 45° C., a pressure in a range of 50 to 150 bar is sufficient to achieve the desired solvent contents.

The gas rate with which the raw material used is treated with liquid or supercritical $CO_2$ is between 2 and 40 kg $CO_2$ per kg product per hour, especially preferably 5 to 20 kg $CO_2$ per kg product per hour. The total amount of $CO_2$ with which the raw material is treated is a function of the type and the amount of impurities to be removed. It is customarily approximately 3 to 30 kg $CO_2$ per kg of raw material used.

BRIEF DESCRIPTION OF THE DRAWINGS

Exemplary devices for carrying out the above-described method are shown in FIGS. 1 and 2.

FIG. 2 shows a crystallization system. Components C, D, E 1 to 4, P and S correspond to those of FIG. 1. In addition, storage container A and pump P 2 are also provided. A solution of the raw material is present in storage container A, which material, in contrast to the system of FIG. 1, is supplied continuously via pump P 2 to container C. The conduction of the $CO_2$ takes place in the same manner as in FIG. 1 so that a countercurrent develops between the solution of the raw material and between the $CO_2$.

Figure 1:
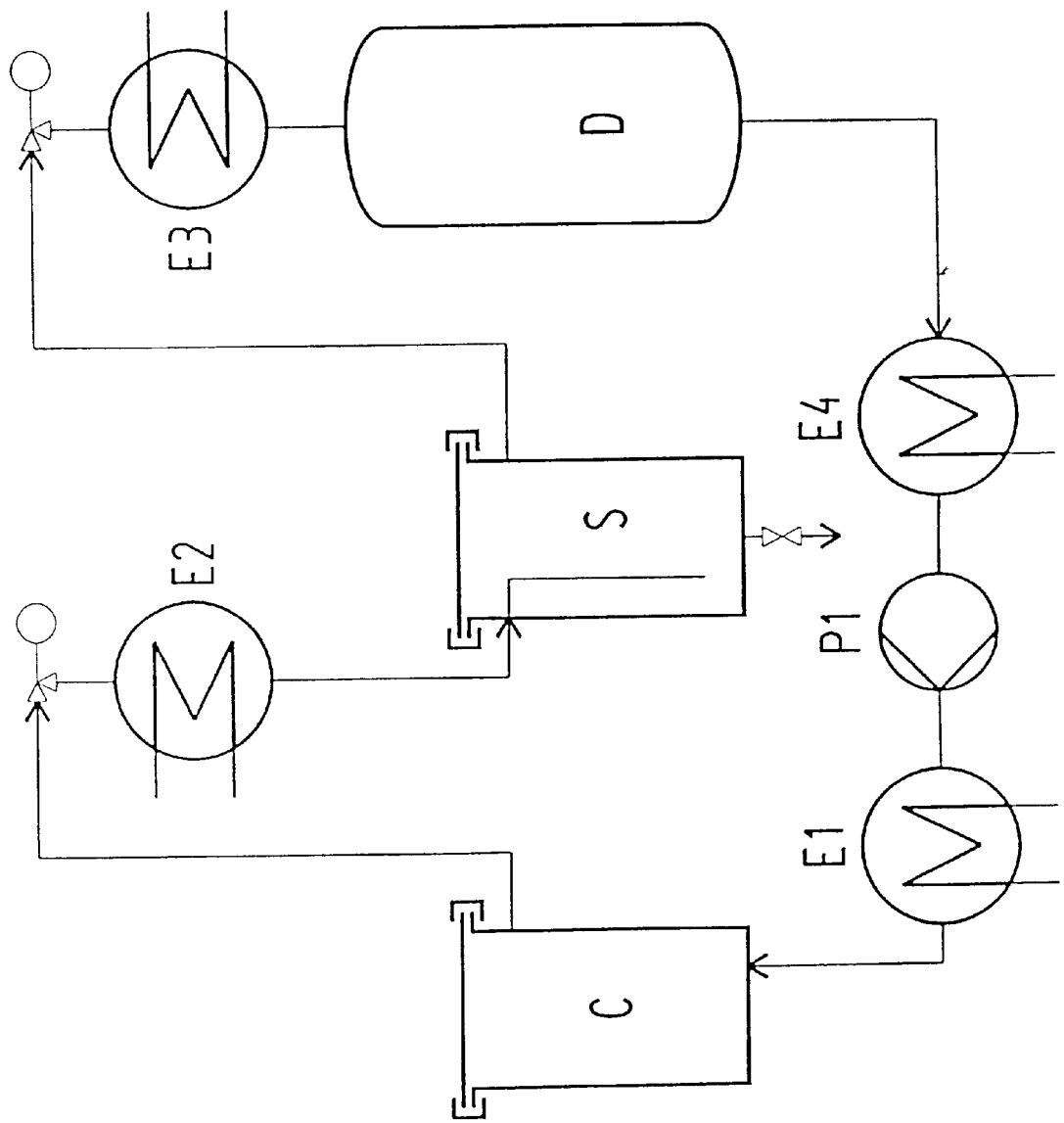
FIG. 1 shows an extraction system. The raw material is placed in container C. Liquid $CO_2$ from collector container D flows to pump P 1, which compresses the $CO_2$ to extraction pressure and transports it through heat exchanger E 1 in which it is heated to extraction temperature into the extractor or into the extraction column. On the way through container C the extractable substances dissolve in the $CO_2$. The $CO_2$ charged with the dissolved substances is conducted to separator S provided with an extract separator (not shown). The dissolving capacity of the $CO_2$ in the separator is decreased by changing the pressure and/or the temperature so that the extracts are separated there. The separation can take place in several stages so that extraction fractions of different qualities are obtained. The gaseous $CO_2$ from separator S is liquefied in a cooled condenser and trapped in collector container D.
Figure 2:
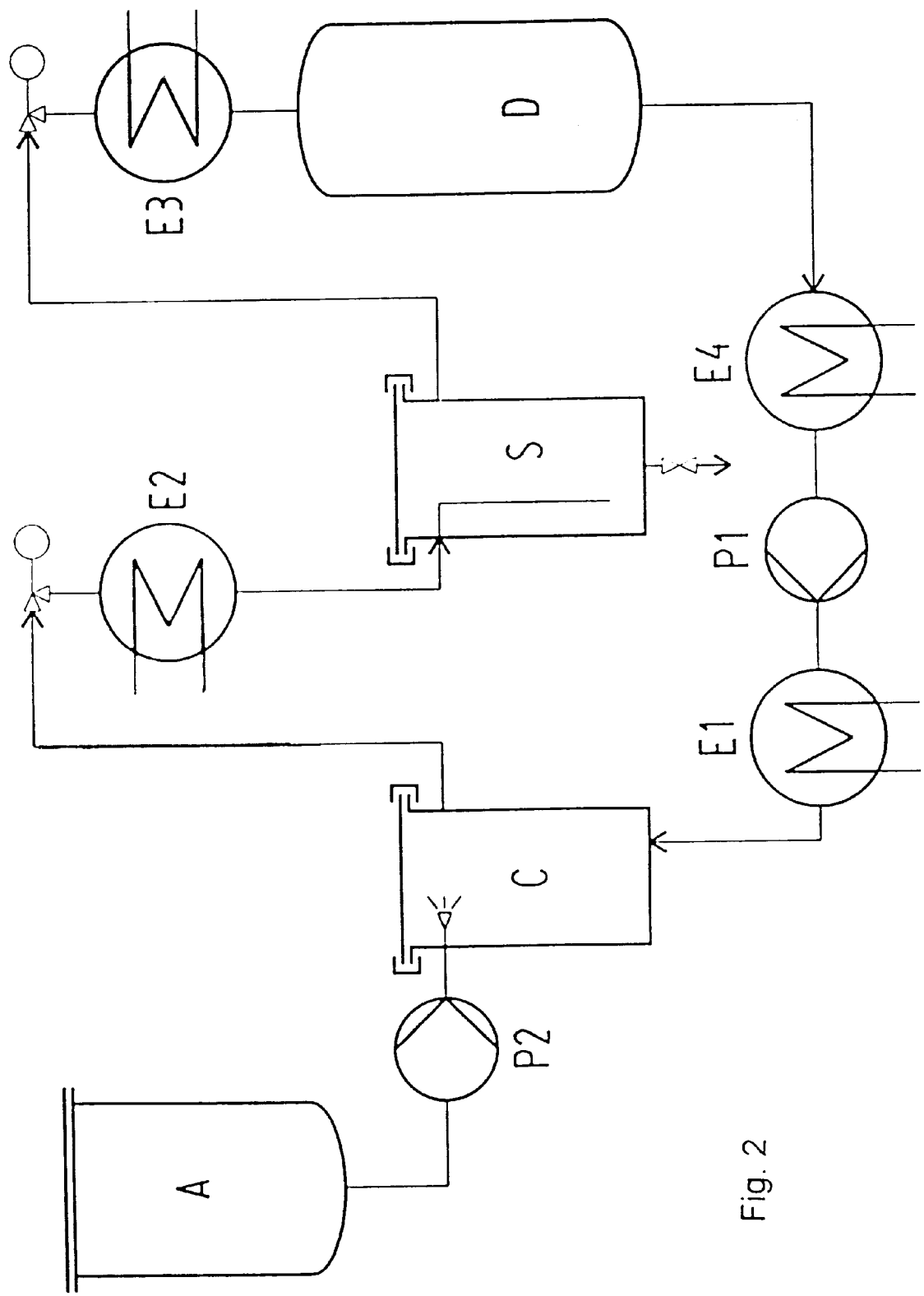
FIG. 2

For measuring the contents of residual solvent the thioctic acid obtained is dissolved in methanol and injected directly into a gas chromatograph. The demonstration takes place by flame ionization detection (FID) according to an internal standard. The demonstration limits are in detail:

| | |
|---|---|
| Cyclohexane | 8 ppm |
| Ethyl acetate | 3 ppm. |

DETAILED DESCRIPTION OF THE INVENTION

The following examples explain the invention in a non-limiting manner.

EXAMPLES 1 TO 7

Two charges from the production of thioctic acid were used as moist solid matter which were crystallized from a mixture of cyclohexane and ethyl acetate and had a residual content of 15% solvent. 3 kg of each of these charges were introduced into the extraction container. Liquid or super-critical $CO_2$ was then made to flow through the thioctic acid from below upward, during which the $CO_2$ was continuously let off into the seperator. After termination of the extraction process the dry product was removed. The test conditions are shown in following table 1 and the results of an analysis of the products obtained in table 2.

TABLE 1

Test conditions

| Example | Charge | T (°C.) | Gas rate (kg/h) | Pressure (bar) | Amount of $CO_2$ (kg) |
|---|---|---|---|---|---|
| 1 | 1 | 25 | 20 | 90 | 30 |
| 2 | 1 | 30 | 20 | 90 | 30 |
| 3 | 1 | 40 | 20 | 90 | 30 |
| 4 | 1 | 40 | 20(30)* | 350(90)* | 30 |
| 5 | 1 | 40 | 20 | 90 | 30 |
| 6 | 2 | 40 | 20 | 90 | 30 |
| 7 | 2 | 40 | 20 | 90 | 30 |

*The gas rate was initially 20 kg/h and the pressure 350 bar. After a throughput of 10 kg $CO_2$ the matter was allowed to stand 30 minutes without a supply of $CO_2$ and then the gas rate elevated to 30 kg/h and the pressure reduced to 90 bar.

The gas rate was initially 20 kg/h and the pressure 350 bar. After a throughput of 10 kg $CO_2$ the matter was allowed to stand 30 minutes without a supply of $CO_2$ and then the gas rate elevated to 30 kg/h and the pressure reduced to 90 bar.

TABLE 2

Results of analysis

| Example | Polymers* (%) | Free SH groups (%) | Residual solvent (ppm) | | Bulk density (kg/l) |
|---|---|---|---|---|---|
| 1 | n.n. | 0,07 | CH: 1010 | EE: 190 | 0,474 |
| 2 | n.n. | 0,08 | CH: 1030 | EE: 197 | 0,486 |
| 3 | n.n. | 0,08 | CH: 491 | EE: 83 | 0,598 |
| 4 | n.n. | 0,08 | CH-. 630 | EE: 118 | 0,600 |
| 5 | n.n. | 0,08 | CH: 487 | EE: 92 | 0,555 |
| 6 | 0,24 | 0,09 | CH: 463 | EE: 105 | 0,594 |
| 7 | 0,20 | 0,09 | CH: 522 | EE: 197 | 0,571 |

*Determined by HPLC
n.n. not demonstratable
CH = Cyclohexane
EE = Ethyl acetate

By way of comparison, cyclohexane contents of only 1500 to 3000 ppm and ethyl-acetate contents of 500 to 1500 ppm are achieved with a traditional drying in a conical screw drying mixer or double-cone drying mixer. It can be seen that the extraction results in a significant improvement.

EXAMPLE 8

A solution of 500 g thioctic acid of charge 2 was produced in 834 g ethyl acetate and placed in the collection container. The solution was then sprayed in two equally large portions under a countercurrent of $CO_2$ in succession into the drying container. The following conditions prevailed in the container:

| | | |
|---|---|---|
| $1^{st}$ portion | temperature | 32 to 36° C. |
| | pressure | 74 to 90 bar |
| | gas rate | 5 kg/h |
| | amount $CO_2$ | 3 kg |
| | time | 23 min |
| $2^{nd}$ portion | temperature | 34° C. |
| | pressure | 69 to 78 bar |
| | gas rate | 10 kg/h |
| | amount $CO_2$ | 6 kg |
| | time | 21 min. |

Subsequently, the gas rate was raised to 20 kg/h and the temperature to 40° C. and a post-extraction carried out for one hour at a pressure of 90 bar under these conditions. Crystalline thioctic acid precipitated in the container which had a very low content of residual solvent, as is shown in table 3. Accordingly, a thioctic acid which is approximately free of cyclohexane can be obtained with high purity with crystallization.

TABLE 3

| | Results of analysis | | | |
|---|---|---|---|---|
| Example | Polymers* (%) | Free SH groups (%) | Residual solvent (ppm) | Bulk density (kg/l) |
| 8 | 0.34 | 0.08 | CH: 8 EE: 225 | 0.474 |

The thioctic acid obtained can be easily processed to ready drug formulations.

What is claimed is:

1. A method of producing dry thioctic acid in which method a raw material in which concentrated thioctic acid is present is treated with liquid or supercritical $CO_2$.

2. The method according to claim 1 in which liquid or supercritical $CO_2$ flows through and/or around solid raw material.

3. The method according to claim 2 in which the raw material is extracted.

4. The method according to claim 1 in which a raw material present in solution is treated in a countercurrent with liquid or supercritical $CO_2$.

5. The method according to claim 1 in which the raw material is crystallized.

6. The method according to claim 5 in which the crystallization is performed from a solvent mixture composed of solvents of the production method for the raw material and of liquid or supercritical $CO_2$.

7. The method according to claim 1 in which the liquid or supercritical $CO_2$ is expanded after flowing through and/or around the raw material, entrained solvent and impurities of the raw material are collected in a catch container and the expanded $CO_2$ gas is then compressed again and made available again for workup.

8. The method according to claim 1 in which the treatment with liquid or supercritical $CO_2$ is carried out at a temperature in a range of 20 to 50° C.

9. The method according to claim 1 in which the treatment with liquid or supercritical $CO_2$ is carried out at a pressure in a range of 50 to 1000 bar.

10. The method according to claim 1 in which the treatment with liquid or supercritical $CO_2$ is carried out at a gas rate in a range of 2 to 40 kg $CO_2$ per kg product per hour.

11. The method according to claim 1 in which 3 to 30 kg $CO_2$ per kg $CO_2$ per kg raw material are used.

12. Thioctic acid with a cyclohexane content of 20 ppm or less.

* * * * *